US00PP32441P2

(12) United States Plant Patent
Star

(10) Patent No.: US PP32,441 P2
(45) Date of Patent: Nov. 10, 2020

(54) ***SANGUISORBA* PLANT NAMED 'RED DREAM'**

(50) Latin Name: *Sanguisorba officinalis*
Varietal Denomination: Red Dream

(71) Applicant: Jan Star, Rijnsburg (NL)

(72) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 16/602,897

(22) Filed: Dec. 19, 2019

(30) Foreign Application Priority Data

Oct. 29, 2019 (QZ) ..... PBR 2019/2750

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05)

(58) Field of Classification Search
USPC ..... Plt./263.1
CPC ..... A01H 6/74
See application file for complete search history.

*Primary Examiner* — Anne Marie Grunberg
(74) *Attorney, Agent, or Firm* — Penny J. Aguirre

(57) ABSTRACT

The new cultivar of *Sanguisorba* plant named 'Red Dream' that is characterized by its flowers that are dark red in color and its floriferous blooming habit.

2 Drawing Sheets

Botanical classification: *Sanguisorba officinalis*.
Variety denomination: 'Red Dream'.

CROSS-REFERENCE TO A RELATED APPLICATION

This application claims priority to European Community Plant Variety Office (CPVO) Plant Breeder's Rights Application No. 2019/2750 filed on Oct. 29, 2019, under 35 U.S.C. 119(f), the entire contents of which is incorporated by reference herein.

BACKGROUND OF THE INVENTION

The present invention relates to a new and distinct cultivar of *Sanguisorba officinalis* and will be referred to hereafter by its cultivar name, 'Red Dream'. 'Red Dream' represents a new Burnet, an herbaceous perennial grown for landscape use.

The inventor discovered the new cultivar, 'Red Dream', as a chance seedling in September of 2017 in Rijnsburg, The Netherlands. The new cultivar was discovered in a production field of *Sanguisorba* 'Arnheim' (not patented) and therefore 'Arnheim' is a probable parent plant.

Asexual propagation of the new cultivar was first accomplished by division in 2017 by the inventor in Rijnsburg, The Netherlands. Asexual propagation by division and terminal stem cuttings has determined that the new cultivar is stable and reproduced true to type in successive generations.

SUMMARY OF THE INVENTION

The following traits have been repeatedly observed and represent the characteristics of the new cultivar. These attributes in combination distinguish 'Red Dream' as a unique cultivar of *Sanguisorba*.

1. 'Red Dream' exhibits flowers that are dark red in color.
2. 'Red Dream' exhibits a floriferous blooming habit.

The likely seed parent of 'Red Dream', 'Arnheim', is similar to 'Red Dream' in plant height and habit. 'Arnheim' differs from 'Red Dream' in having flowers that are smaller in size and more rose pink in color. 'Red Dream' can be most closely compared to *Sanguisorba officinalis* cultivars 'Red Thunder' (not patented) and 'Tanna' (not patented). Both a similar to 'Red Dream' in having inflorescences that are red in color. 'Red Thunder' differs from 'Red Dream' in having weaker stems that are not held upright without support and inflorescences that are slightly more burgundy in color. 'Tanna' differs from 'Red Dream' in having a smaller plant height, more fern-like foliage, and inflorescences that are more pink-red in color.

BRIEF DESCRIPTION OF THE DRAWINGS

The accompanying colored photographs illustrate the overall appearance and distinct characteristics of the new *Echinacea*. The photographs were taken of a one-year-old plant of the new cultivar as field grown in Rijnsburg, The Netherlands and placed in a 28-cm container for the photographs.

The photograph in FIG. 1 illustrates the overall habit and appearance of 'Red Dream' in bloom.

Figure 1:
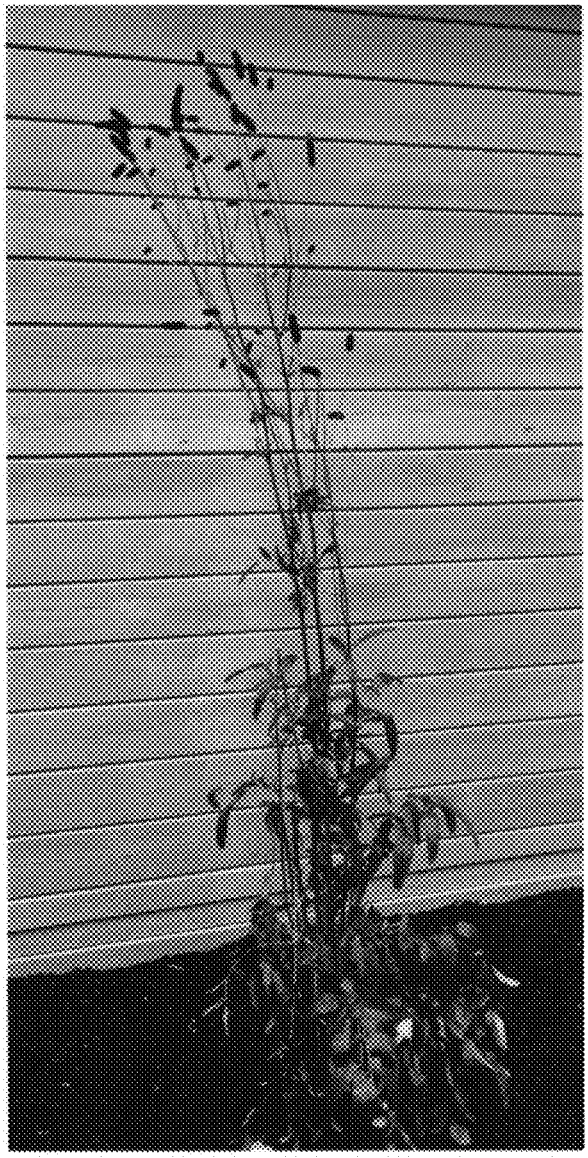
Figure 2:
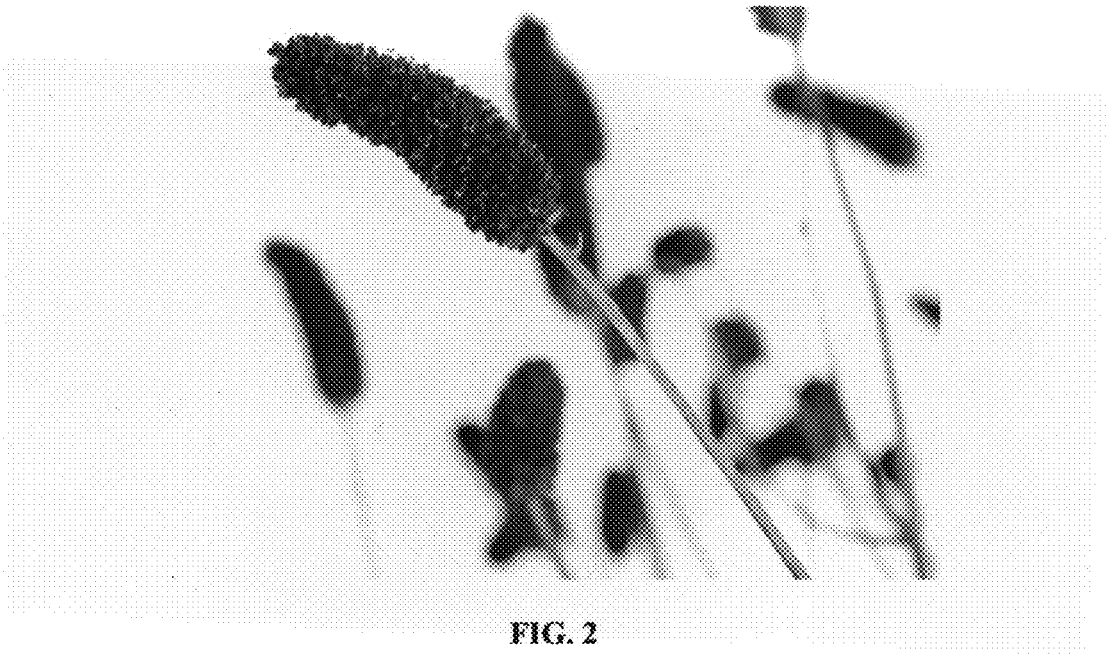

The photograph in FIG. 2 provides a close-up view of an inflorescence of 'Red Dream'.

Figure 3:
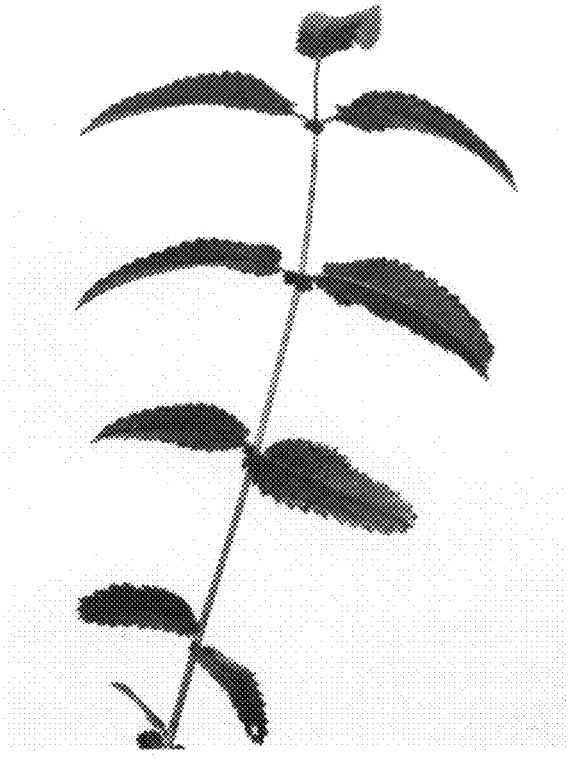

The photograph in FIG. 3 provides a close-up view of the foliage of 'Red Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July through August in The Netherlands.

*Plant habit*.—Herbaceous perennial.

*Height and spread*.—Average of 1 m in height from soil level to top of foliar plane, 1.32 m in height from soil level to top of floral plane, 89.5 cm in spread as a one-year-old field grown plant.

*Hardiness*.—At least in U.S.D.A. Zones 4 to 9.

*Diseases and pests*.—No susceptibility or resistance to diseases or pests has been observed.

*Root description*.—Moderately fibrous, freely branched, main roots are an average of 3 mm in diameter, 164C in color.

*Propagation*.—Terminal stem cuttings and division.

*Root initiation*.—Develop in 7 to 10 days under greenhouse conditions under mist at 21° to 23° C.

*Time required for root development*.—1 month to fully develop a 32-cell liner.

*Growth rate*.—Vigorous.

Stem description:

*Shape*.—Round, slightly angled.

*Stem color*.—Young; 144A, mature: 144A and 146A.

*Stem size*.—Up to 91.8 cm in length and 4 mm in diameter.

*Stem aspect*.—Average of 15° to vertical.

*Stem surface*.—Slightly glossy.

*Internode length*.—Up to 16 cm.

*Branching*.—Average of basal 15 branches, with moderate development of lateral branches; an average of 15 per plant.

Foliage description:

*Leaf shape*.—Obovate.

*Leaf division*.—Compound; an average of 11 leaflets per leaf (ranges from 13 leaflets on lower leaves to 5 leaflets on upper leaves.

*Leaf base*.—Truncate.

*Leaf apex*.—Acute.

*Leaf aspect*.—Average of 30°.

*Leaf arrangement*.—Alternate.

*Leaf size*.—Average of 19 cm in length (including petiole), 12.7 cm in width.

*Leaf attachment*.—Petiolate.

*Leaflet*.—Lanceolate to nearly oblong in shape, terminal leaflets; average of 6.6 cm in length and width, lateral leaflets; average of 5 cm in length and width, acute apex, truncate base.

*Leaflet venation*.—Pinnate, upper and lower surface; conspicuous, 148B.

*Leaflet margins*.—Serrate to crenate.

*Leaflet surface*.—Both surfaces smooth and glabrous, glossy and non-rugose.

*Leaflet color*.—Young; upper surface a color between NN137A and 147A, lower surface 137B, mature; upper surface NN137A, lower surface a color between 138A and 147B.

*Rachis (petiole) and petiolule*.—Rachis (petiole); average of 10.9 cm in length, 1.75 mm in diameter, petiolule; average of 1.1 cm in length and 0.9 mm in diameter, moderately glossy, strong, upper surface color 146A, tinged at node with 183C, lower surface color 144A.

*Stipules*.—At the base of each leaf is a leafy stipule on each side, broadly falcate in shape, 3.4 cm in length, 1.6 cm in width, surfaces smooth and glabrous, crenate margins, color upper surface NN137A, lower surface a color between 138A and 147B.

Inflorescence description:

*Type*.—Terminal spikes of numerous, densely packed flowers in elongated ovoid to oblong shaped inflorescence, determinate.

*Inflorescence size*.—Average of 3 cm in height and 1.2 cm in diameter.

*Fragrance*.—Faint and unpleasant.

*Flower lastingness*.—About 14 days, persistent.

*Flower quantity*.—Average of 150 flowers per spike, over 30,000 flowers and buds per plant.

*Flower aspect*.—Rotate, single, outward and freely flowering.

*Flower size*.—Average of 4.5 mm in height and diameter, 4 mm in depth.

*Peduncle*.—Average of 40.1 cm in length, 3 mm in diameter, held straight up, strong, smooth and glabrous, slightly glossy, 143A in color.

*Bud description*.—Average of 2.5 mm in length, 2 mm in diameter, orbicular in shape, smooth, glabrous, and matte surface, color; 60B, apex 187A, base 144C.

*Petals*.—Rotate, cruciform, average of 4, 1 row, unfused, 3 mm in length, 2 mm in width, ovate in shape, acute tip, cuneate base, entire margins, both surfaces glabrous, slightly velvety and matte, color; when opening upper surface N155A with tip strongly tinged 60D, central band of a color darker than 147A, when opening lower surface 60B with tip strongly tinged with 187A and base 145D, when fully open upper surface 61B with base 150D with a central band of 147B, outer tip 147A, then changing to 60A, fully open lower surface 61C, changing to 145D at the base with a band of N186C then changing to 60A, 145D at base with central band N186C.

*Calyx*.—Rotate, cruciform, average of 3 mm in length and diameter.

*Sepal*.—An average of 4 in 1 row, average of 2 mm in length and 1 mm in width, narrow ovate in shape, acute tip, cuneate base, entire margins, both surfaces matte and moderately pubescent with short adpressed hairs; average of 0.3 mm in length and too small to measure color, color; when opening upper and lower surface N199D, fully open upper and lower surface N199D with apex N199C.

*Flower bracts*.—None.

Reproductive organs.

*Gynoecium*.—Pistil: 1, average of 1.5 mm in length, stigma is flattened and club-shaped, 5 mm in length and diameter, 59A in color, style; average of 1.25 mm in length, 59C in color, ovary; 145C in color.

*Androecium*.—Stamens; average of 4, filament; 2.25 mm in length, NN155D in color, anthers; broad oblong in shape, 0.3 mm in length, 0.2 mm in width, pollen; low in quantity, 11B in color.

*Fruit/seed*.—None observed to date.

It is claimed:

1. A new and distinct cultivar of *Sanguisorba* plant named 'Red Dream' as herein illustrated and described.

* * * * *